(12) United States Patent
Singh et al.

(10) Patent No.: US 11,324,484 B2
(45) Date of Patent: *May 10, 2022

(54) MULTI-STAGE TRANS-IMPEDANCE AMPLIFIER (TIA) FOR AN ULTRASOUND DEVICE

(71) Applicant: BFLY Operations, Inc., Guilford, CT (US)

(72) Inventors: Amandeep Singh, Jersey City, NJ (US); Kailiang Chen, Branford, CT (US); Tyler S. Ralston, Clinton, CT (US)

(73) Assignee: BFLY OPERATIONS, INC., Guilford, CT (US)

( * ) Notice: Subject to any disclaimer, the term of this patent is extended or adjusted under 35 U.S.C. 154(b) by 680 days.

This patent is subject to a terminal disclaimer.

(21) Appl. No.: 16/011,715

(22) Filed: Jun. 19, 2018

(65) Prior Publication Data

US 2018/0360426 A1    Dec. 20, 2018

Related U.S. Application Data

(60) Provisional application No. 62/522,597, filed on Jun. 20, 2017.

(51) Int. Cl.
*B06B 1/06* (2006.01)
*A61B 8/08* (2006.01)
(Continued)

(52) U.S. Cl.
CPC .......... *A61B 8/5207* (2013.01); *A61B 8/4483* (2013.01); *A61B 8/54* (2013.01);
(Continued)

(58) Field of Classification Search
None
See application file for complete search history.

(56) References Cited

U.S. PATENT DOCUMENTS

| 4,829,491 A | 5/1989 | Saugeon et al. |
| 5,585,626 A | 12/1996 | Beck et al. |

(Continued)

FOREIGN PATENT DOCUMENTS

| CN | 103607130 A | 2/2014 |
| CN | 104242937 A | 12/2014 |

(Continued)

OTHER PUBLICATIONS

Jiajian, Yao. "Time-gain-compensation amplifier for ultrasonic echo signal processing." Thesis Report. (2010). (Year: 2010).*

(Continued)

*Primary Examiner* — Isam A Alsomiri
*Assistant Examiner* — Jonathan D Armstrong
(74) *Attorney, Agent, or Firm* — Osha Bergman Watanabe & Burton LLP

(57) ABSTRACT

An ultrasound circuit comprising a multi-stage trans-impedance amplifier (TIA) is described. The TIA is coupled to an ultrasonic transducer to amplify an electrical signal generated by the ultrasonic transducer in response to receiving an ultrasound signal. The TIA may include multiple stages, at least two of which operate with different supply voltages. The TIA may be followed by further processing circuitry configured to filter, amplify, and digitize the signal produced by the TIA.

20 Claims, 3 Drawing Sheets

(51) Int. Cl.
  *A61B 8/00* (2006.01)
  *H03F 3/50* (2006.01)
  *H03F 3/45* (2006.01)

(52) U.S. Cl.
  CPC ........... *A61B 8/56* (2013.01); *H03F 3/45475* (2013.01); *H03F 3/50* (2013.01); *H03F 2200/411* (2013.01); *H03F 2200/516* (2013.01); *H03F 2203/45512* (2013.01)

(56) References Cited

U.S. PATENT DOCUMENTS

| | | | | |
|---|---|---|---|---|
| 5,610,709 | A * | 3/1997 | Arrington | G01J 1/42 |
| | | | | 356/218 |
| 5,684,431 | A * | 11/1997 | Gilbert | H03G 7/06 |
| | | | | 330/254 |
| 5,844,445 | A | 12/1998 | Takeyari | |
| 6,356,152 | B1 | 3/2002 | Jezdic et al. | |
| 6,404,281 | B1 | 6/2002 | Kobayashi | |
| 6,806,744 | B1 * | 10/2004 | Bell | H03K 5/2481 |
| | | | | 327/53 |
| 6,826,369 | B1 * | 11/2004 | Bondarev | H04B 10/1143 |
| | | | | 398/106 |
| 7,313,053 | B2 | 12/2007 | Wodnicki | |
| 7,449,958 | B1 | 11/2008 | Voo | |
| 7,605,660 | B1 | 10/2009 | Kobayashi | |
| 8,662,395 | B2 | 3/2014 | Melandso et al. | |
| 8,852,103 | B2 | 10/2014 | Rothberg et al. | |
| 9,087,223 | B2 * | 7/2015 | Tualle | G06G 7/1928 |
| 9,229,097 | B2 | 1/2016 | Rothberg et al. | |
| 9,473,136 | B1 | 10/2016 | Chen et al. | |
| 9,492,144 | B1 | 11/2016 | Chen et al. | |
| 9,521,991 | B2 | 12/2016 | Rothberg et al. | |
| 9,592,030 | B2 | 3/2017 | Rothberg et al. | |
| 9,705,518 | B2 | 7/2017 | Chen et al. | |
| 9,933,516 | B2 | 4/2018 | Chen et al. | |
| 9,958,537 | B1 | 5/2018 | Chen et al. | |
| 10,014,871 | B2 | 7/2018 | Chen et al. | |
| 10,082,488 | B2 | 9/2018 | Chen et al. | |
| 10,082,565 | B2 | 9/2018 | Chen et al. | |
| 10,116,263 | B1 * | 10/2018 | Broekaert | H03F 3/45179 |
| 10,187,020 | B2 * | 1/2019 | Chen | G01S 7/52025 |
| 10,231,713 | B2 | 3/2019 | Chen et al. | |
| 10,263,031 | B2 * | 4/2019 | Wang | H01L 27/14612 |
| 10,340,866 | B2 * | 7/2019 | Singh | H03F 3/345 |
| 10,340,867 | B2 | 7/2019 | Singh et al. | |
| 10,840,864 | B2 | 11/2020 | Singh et al. | |
| 10,857,567 | B2 | 12/2020 | Singh et al. | |
| 2001/0038450 | A1 * | 11/2001 | McCaffrey | G01N 21/763 |
| | | | | 356/311 |
| 2003/0025562 | A1 * | 2/2003 | Andreou | H03F 3/45475 |
| | | | | 330/308 |
| 2004/0119587 | A1 * | 6/2004 | Davenport | G08B 29/10 |
| | | | | 340/538 |
| 2004/0260214 | A1 * | 12/2004 | Echt | A61H 31/006 |
| | | | | 601/46 |
| 2005/0148878 | A1 | 7/2005 | Phelps et al. | |
| 2005/0175350 | A1 * | 8/2005 | Hartzell | H05K 1/0254 |
| | | | | 398/135 |
| 2006/0161359 | A1 * | 7/2006 | Lalla | G01F 1/8431 |
| | | | | 702/65 |
| 2006/0164169 | A1 * | 7/2006 | Meek | H03F 3/195 |
| | | | | 330/297 |
| 2006/0273805 | A1 * | 12/2006 | Peng | G01R 27/2605 |
| | | | | 324/686 |
| 2007/0001764 | A1 * | 1/2007 | Huang | H03F 3/45183 |
| | | | | 330/261 |
| 2007/0038091 | A1 * | 2/2007 | Shiki | A61B 8/4494 |
| | | | | 600/437 |
| 2007/0086311 | A1 * | 4/2007 | Higashiyama | H03F 3/087 |
| | | | | 369/120 |
| 2007/0232917 | A1 | 10/2007 | Bae et al. | |
| 2007/0242567 | A1 | 10/2007 | Daft et al. | |
| 2007/0287923 | A1 | 12/2007 | Adkins et al. | |
| 2008/0272848 | A1 * | 11/2008 | Sutardja | H03F 3/08 |
| | | | | 330/297 |
| 2009/0002073 | A1 * | 1/2009 | Kim | H03G 11/002 |
| | | | | 330/279 |
| 2009/0157130 | A1 * | 6/2009 | Ideker | A61N 1/3906 |
| | | | | 607/5 |
| 2009/0250729 | A1 | 10/2009 | Lemmerhirt et al. | |
| 2010/0152587 | A1 | 6/2010 | Haider et al. | |
| 2010/0166228 | A1 * | 7/2010 | Steele | H04R 3/00 |
| | | | | 381/113 |
| 2010/0234736 | A1 * | 9/2010 | Corl | G10K 11/355 |
| | | | | 600/463 |
| 2010/0237807 | A1 | 9/2010 | Lemmerhirt | |
| 2010/0246648 | A1 * | 9/2010 | Rocamora | H04B 3/56 |
| | | | | 375/222 |
| 2010/0254547 | A1 * | 10/2010 | Grosh | H01L 41/083 |
| | | | | 381/114 |
| 2010/0317972 | A1 | 12/2010 | Baumgartner et al. | |
| 2011/0115562 | A1 * | 5/2011 | Gilbert | H03F 3/2171 |
| | | | | 330/262 |
| 2011/0130109 | A1 | 6/2011 | Ogasawara | |
| 2012/0163129 | A1 | 6/2012 | Antoine et al. | |
| 2012/0265491 | A1 * | 10/2012 | Drummy | G01N 27/9073 |
| | | | | 702/189 |
| 2013/0056622 | A1 * | 3/2013 | Tualle | G06G 7/1928 |
| | | | | 250/214.1 |
| 2013/0064043 | A1 | 3/2013 | Degertekin et al. | |
| 2014/0240482 | A1 | 8/2014 | Ikeda et al. | |
| 2014/0288428 | A1 | 9/2014 | Rothberg et al. | |
| 2015/0032002 | A1 * | 1/2015 | Rothberg | A61B 8/4488 |
| | | | | 600/440 |
| 2015/0086221 | A1 * | 3/2015 | Shringarpure | H03F 3/45475 |
| | | | | 398/208 |
| 2015/0145597 | A1 | 5/2015 | Huang et al. | |
| 2015/0280662 | A1 | 10/2015 | Nimran et al. | |
| 2015/0297193 | A1 | 10/2015 | Rothberg et al. | |
| 2015/0298170 | A1 | 10/2015 | Rothberg et al. | |
| 2015/0374335 | A1 | 12/2015 | Brown et al. | |
| 2016/0228099 | A1 | 8/2016 | Matsumura | |
| 2017/0026011 | A1 * | 1/2017 | Khaw | H03F 3/08 |
| 2017/0143306 | A1 | 5/2017 | Rothberg et al. | |
| 2017/0160239 | A1 | 6/2017 | Chen et al. | |
| 2017/0160387 | A1 | 6/2017 | Chen et al. | |
| 2017/0160388 | A1 | 6/2017 | Chen et al. | |
| 2017/0163225 | A1 | 6/2017 | Chen et al. | |
| 2017/0163276 | A1 | 6/2017 | Chen et al. | |
| 2017/0202541 | A1 | 7/2017 | Ralston | |
| 2017/0264307 | A1 | 9/2017 | Chen et al. | |
| 2017/0279423 | A1 * | 9/2017 | Ko | H03F 3/265 |
| 2017/0296145 | A1 | 10/2017 | Rothberg et al. | |
| 2017/0307739 | A1 | 10/2017 | Chen et al. | |
| 2018/0070925 | A1 | 3/2018 | Chen et al. | |
| 2018/0210073 | A1 | 7/2018 | Chen et al. | |
| 2018/0360426 | A1 * | 12/2018 | Singh | A61B 8/54 |
| 2018/0361431 | A1 | 12/2018 | Singh et al. | |
| 2018/0367110 | A1 * | 12/2018 | Singh | G01N 29/449 |
| 2018/0367111 | A1 | 12/2018 | Singh et al. | |
| 2019/0050618 | A1 * | 2/2019 | Khuri-Yakub | A61B 5/1172 |
| 2019/0131939 | A1 * | 5/2019 | Shapoury | H03F 3/2176 |
| 2019/0140603 | A1 * | 5/2019 | Chen | A61B 5/6801 |
| 2019/0142389 | A1 * | 5/2019 | Singh | H03F 3/45475 |
| | | | | 600/437 |
| 2019/0149109 | A1 * | 5/2019 | Singh | G01N 29/449 |
| | | | | 367/135 |
| 2019/0149110 | A1 | 5/2019 | Singh et al. | |
| 2020/0195210 | A1 * | 6/2020 | Tanaka | H03F 1/302 |

FOREIGN PATENT DOCUMENTS

| | | |
|---|---|---|
| CN | 105555199 | 5/2016 |
| TW | 201445554 A | 12/2014 |
| WO | WO 2007/096636 | 8/2007 |
| WO | WO 2010/064000 A2 | 6/2010 |
| WO | WO 2017/048549 A1 | 3/2017 |
| WO | WO 2018/236778 A1 | 12/2018 |
| WO | WO 2018/236779 A1 | 12/2018 |

(56) References Cited

FOREIGN PATENT DOCUMENTS

WO   WO 2018/236786 A1   12/2018
WO   WO 2018/236799 A1   12/2018

OTHER PUBLICATIONS

International Preliminary Report on Patentability dated Jan. 2, 2020 in connection with International Application No. PCT/US2018/038147.
Jiajian, Time-gain-compensation amplifier for ultrasonic echo signal processing. Faculty of EEMCS, Delft University of Technology, in partial fulfillment of MSc. Degree 2010: 1-81.
Kim, Fully Integrated CMOS Ultrasound Transceiver Chip for High-Frequency High-Resolution Ultrasonic Imaging Systems. PhD Dissertation. The Pennsylvania State University College of Engineering. Dec. 2009; 157 pages.
Wygant et al. A miniature real-time volumetric ultrasound imaging system. Medical Imaging 2005: Ultrasonic Imaging and Signal Processing. vol. 5750. International Society for Optics and Photonics, 2005; 12 pages.
International Search Report and Written Opinion dated Feb. 7, 2017 for Application No. PCT/US2016/064314.
International Preliminary Report on Patentability dated Jun. 14, 2018 in connection with International Application No. PCT/US2016/064314.
International Search Report and Written Opinion dated Aug. 30, 2018 in connection with International Application No. PCT/US2018/038147.
International Search Report and Written Opinion dated Sep. 6, 2018 in connection with International Application No. PCT/US2018/038180.
Taiwanese Office Action dated Jan. 19, 2018 in connection with Taiwanese Application No. 105139662.
Agarwal et al., Single-Chip Solution for Ultrasound Imaging Systems: Initial Results. 2007 IEEE Ultrasonics Symposium. Oct. 1, 2007;1563-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012; 173-6.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Daft et al., A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Doody et al., Modeling and Characterization of CMOS-Fabricated Capacitive Micromachined Ultrasound Transducers. J Microelectromechan Sys. Feb. 2011;20(1):104-118.

Gurun et al., Front-end CMOS electronics for monolithic integration with CMUT arrays: circuit design and initial experimental results. Proc Ultrason Symp. 2008;390-3.
Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.
Kim et al., Design and Test of A Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.
Kupnik et al., Wafer-bonded CMUT meets CMOS. MEMS-based Ultrasonic Transducer Arrays including Electronics Integration. 2010 CMOS Emerging Technology Workshop. Whistler, Canada. May 21, 2010. 22 pages.
Orozco, Programmable-Gain Transimpedance Amplifiers Maximize Dynamic Range in Spectroscopy Systems. Analog Dialogue. May 2013;47(05):1-5.
Extended European Search Report dated Feb. 11, 2021 in connection with European Application No. 18821113.0.
Extended European Search Report dated Jan. 27, 2021 in connection with European Application No. 18829732.8.
Extended European Search Report dated Feb. 15, 2021 in connection with European Application No. 18820523.1.
Extended European Search Report dated Feb. 12, 2021 in connection with European Application No. 18820178.4.
Cenkeramaddi et al., Inverter-based 1V Transimpedance Amplifier in 90nm CMOS for Medical Ultrasound Imaging. NORCHIP. Nov. 16, 2009; pp. 1-4.
Gurun et al., Front-End Receiver Electronics for High-Frequency Monolithic CMUT-on-CMOS Imaging Arrays. IEEE Transactions of Ultrasonics, Ferroelectrics, and Frequency Control. Aug. 1, 2011; 58(8): 1658-68.
Huang et al., A High-frequency Transimpedance Amplifier for CMOS Integrated 2D CMUT Array towards 3D Ultrasound Imaging. Engineering in Medicine and Biology Society (EMBC). 2013 34th annual International Conference of the IEEE. Jul. 3, 2013; pp. 101-104.
Lim et al., Towards a Reduced-Wire Interface for CMUT-Based Intravascular Ultrasound Imaging Systems. IEEE Transacitons on Biomedical Circuits and Systems. Apr. 1, 2017; 11(2):400-410.
Wygant et al., An Integrated Circuit With Transmit Beamforming Flip-Chip Bonded to a 2-D CMUT Array for 3-D Ultrasound Imaging. IEEE Transactions on Ultrasonics, Ferroelectrics, and Frequency Control. Oct. 1, 2009; 56(10):2145-2156.
Wygant et al., Integration of 2D CMUT arrays with Front-End Electronics for Volumetric Ultrasound Imaging. IEEE Transactions on Ultrasonics, Ferroelectrics and Frequency Control. Feb. 1, 2008; 55(2):327-342.
Office Action issued in Chinese Application No. 201880040114.5, dated Dec. 23, 2021 (13 pages).
E. Säckinger et al., "The Transimpedance Limit", IEEE Transactions on Circuits and Systems, Aug. 2010, vol. 57, No. 8, pp. 1848-1856 (9 pages).
E. Kang et al., "A Variable-Gain Low-Noise Transimpedance Amplifier for Miniature Ultrasound Probes", IEEE Journal of Solid-State Circuits, Dec. 2020, vol. 55, No. 12, pp. 3157-3168 (12 pages).

\* cited by examiner

MULTI-STAGE TRANS-IMPEDANCE AMPLIFIER (TIA) FOR AN ULTRASOUND DEVICE

CROSS-REFERENCE TO RELATED APPLICATIONS

This Application claims the benefit under 35 U.S.C. § 119(e) of U.S. Provisional Application Ser. No. 62/522,597, filed Jun. 20, 2017 and entitled "MULTI-STAGE TRANS-IMPEDANCE AMPLIFIER (TIA) FOR AN ULTRASOUND DEVICE," which is hereby incorporated herein by reference in its entirety.

BACKGROUND

Field

The present application relates to ultrasound devices having an amplifier for amplifying received ultrasound signals.

Related Art

Ultrasound probes often include one or more ultrasound sensors which sense ultrasound signals and produce corresponding electrical signals. The electrical signals are processed in the analog or digital domain. Sometimes, ultrasound images are generated from the processed electrical signals.

BRIEF SUMMARY

According to an aspect of the present application, an ultrasound apparatus is provided, comprising an ultrasound sensor and a multi-stage trans-impedance amplifier (TIA) coupled to the ultrasound sensor and configured to receive and amplify an output signal from the ultrasound sensor. The multi-stage TIA may include stages operating with different supply voltages, which may reduce power consumption in at least some situations.

According to an aspect of the present application, an ultrasound apparatus is provided, comprising an ultrasonic transducer and a multi-stage trans-impedance amplifier (TIA) having a input terminal coupled to the ultrasonic transducer. The multi-stage TIA is configured to receive and amplify an analog electrical signal from the ultrasonic transducer. The multi-stage TIA comprises a first stage configured to receive a first supply voltage and a second stage configured to receive a second supply voltage different than the first supply voltage.

According to an aspect of the present application, an ultrasound on a chip device is provided, comprising a substrate, a plurality of ultrasonic transducers integrated on the substrate, and analog processing circuitry integrated on the substrate and coupled to the plurality of ultrasonic transducers. The analog processing circuitry comprises a multi-stage trans-impedance amplifier coupled to an ultrasonic transducer of the plurality of ultrasonic transducers. The multi-stage TIA comprises multiple stages configured to receive different supply voltages.

According to an aspect of the present application, a method of operating an ultrasound circuit is provided, comprising receiving and amplifying, with a first stage of a multi-stage trans-impedance amplifier, an electrical signal output by a an ultrasonic transducer, the first stage of the multi-stage TIA operating at a first supply voltage value, and amplifying, with a second stage of the multi-stage TIA operating at a second supply voltage value different than the first supply voltage value, an output signal of the first stage.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present application relate to amplification circuitry for an ultrasound device. An ultrasound device may include one or more ultrasonic transducers configured to receive ultrasound signals and produce electrical output signals. Thus, the ultrasonic transducers may be operated as ultrasound sensors. The ultrasound device may include one or more amplifiers for amplifying the electrical output signals. In some embodiments, the amplifier(s) may be multi-stage amplifiers, with stages that operate at different supply voltage levels. In this manner, a lower supply voltage level may be used for at least one of the stages, thus facilitating lower power operation. In some embodiments, the first stage of the multi-stage amplifier may operate with a lower supply voltage than a following stage. The following stage may provide a desired output gain of the amplifier.

According to an aspect of the present application, a method of operating an ultrasound circuit is provided, comprising producing an electrical signal with an ultrasonic transducer and amplifying the electrical signal with a multi-stage TIA. The multi-stage TIA may include a first stage configured to operate at a lower supply voltage level than a following stage, and thus may provide power savings.

The aspects and embodiments described above, as well as additional aspects and embodiments, are described further below. These aspects and/or embodiments may be used individually, all together, or in any combination of two or more, as the application is not limited in this respect.

Figure 1:
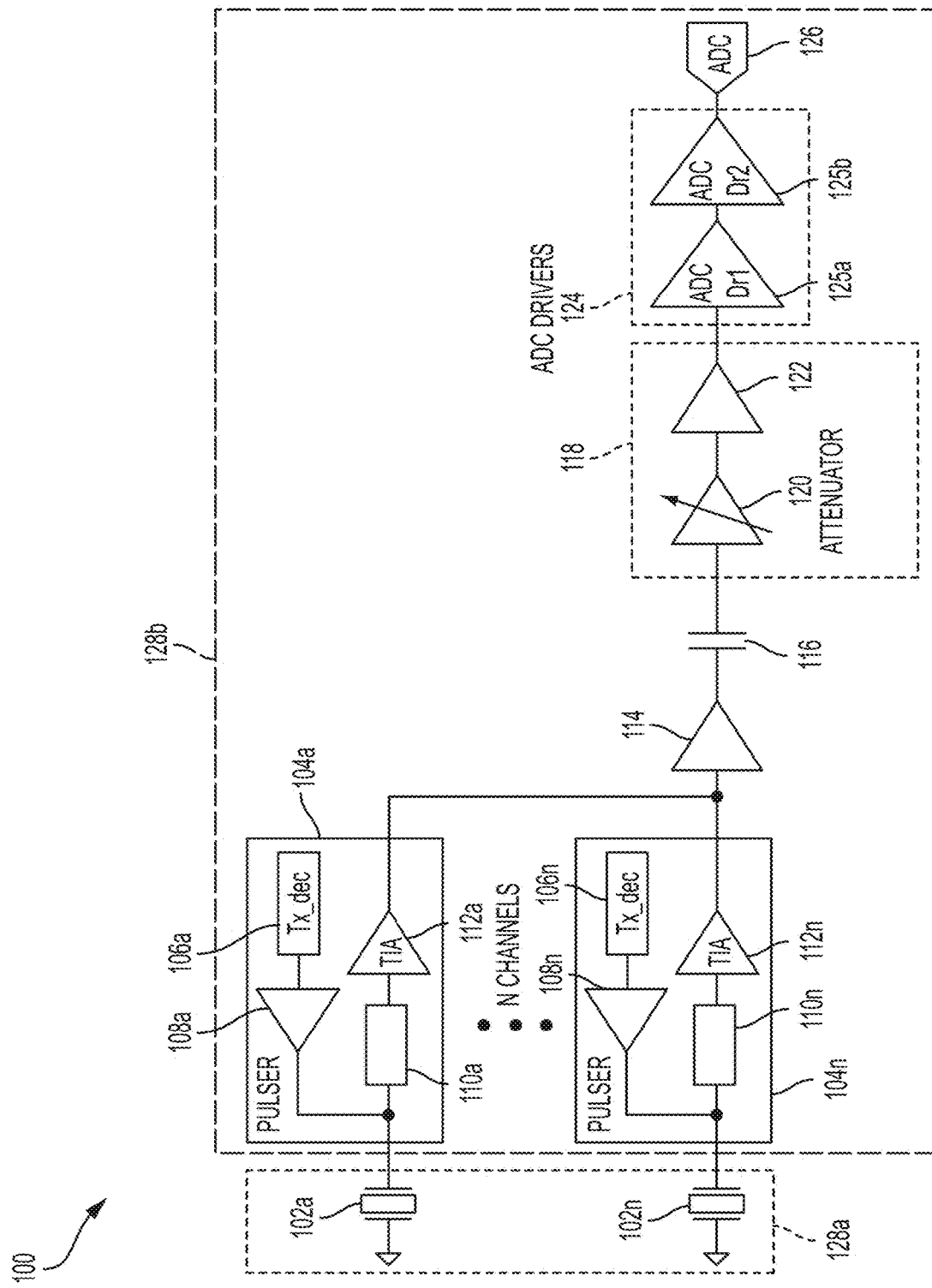
FIG. 1 is a block diagram of an ultrasound device including an amplifier for amplifying an ultrasound signal, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Alternative types of ultrasonic transducers may be used in other embodiments.

The circuit 100 further comprises N circuitry channels 104a ... 104n. The circuitry channels may correspond to a respective ultrasonic transducer 102a ... 102n. For example, there may be eight ultrasonic transducers 102a ... 102n and eight corresponding circuitry channels 104a ... 104n. In some embodiments, the number of ultrasonic transducers 102a ... 102n may be greater than the number of circuitry channels.

The circuitry channels 104a ... 104n may include transmit circuitry, receive circuitry, or both. The transmit circuitry may include transmit decoders 106a ... 106n coupled to respective pulsers 108a ... 108n. The pulsers 108a ... 108n may control the respective ultrasonic transducers 102a ... 102n to emit ultrasound signals.

The receive circuitry of the circuitry channels 104a ... 104n may receive the (analog) electrical signals output from respective ultrasonic transducers 102a ... 102n. In the illustrated example, each circuitry channel 104a ... 104n includes a respective receive circuit 110a ... 110n and an amplifier 112a ... 112n. The receive circuit 110a ... 110n may be controlled to activate/deactivate readout of an electrical signal from a given ultrasonic transducer 102a ... 102n. An example of suitable receive circuits 110a ... 110n are switches. That is, in one embodiment the receive circuits are controllable switches which are switched during transmit mode to disconnect the ultrasonic transducers from the receive circuitry and during receive mode to connect the ultrasonic transducers to the receive circuitry. Alternatives to a switch may be employed to perform the same function.

The amplifiers 112a ... 112n may be multi-stage TIAs in some embodiments, outputting amplified analog signals. As will be described further below, in some embodiments one or more—and in some embodiments all—of the amplifiers 112a-112n may include a first stage operating at a lower supply voltage level than a subsequent stage. The use of multi-stage TIAs with multiple supply voltages may facilitate low power operation of the circuit 100 compared to the use of alternative amplifier designs.

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a ... 112n and may provide an averaged output signal. The averaged output signal may be formed in part by adding or subtracting the signals from the various amplifiers 112a ... 112n. The averaging circuit 114 may include a variable feedback resistance. The value of the variable feedback resistance may be adjusted dynamically based upon the number of amplifiers 112a ... 112n from which the averaging circuit receives signals. In some embodiments, the variable resistance may include N resistance settings. That is, the variable resistance may have a number of resistance settings corresponding to the number of circuitry channels 104a ... 104n. Thus, the average output signal may also be formed in part by application of the selected resistance to the combined signal received at the input(s) of the averaging circuit 114.

The averaging circuit 114 is coupled to an auto-zero block 116, also referred to herein as a "DC block." The auto-zero block 116 may filter the averaged signal provided by the averaging circuit 114, and thus may be considered a filter in at least some embodiments.

The auto-zero block 116 is coupled to a programmable gain amplifier 118 which includes an attenuator 120 and a fixed gain amplifier 122. The programmable gain amplifier 118 may perform time gain compensation (TGC), and thus may alternatively be referred to as a TGC stage or circuit. In performing TGC, the programmable gain amplifier 118 may increase the amplification provided during reception of an ultrasound signal by an ultrasonic transducer, thus compensating for the natural attenuation of the signal which occurs over time.

The programmable gain amplifier 118 is coupled to an ADC 126 via ADC drivers 124. In the illustrated example, the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the amplifiers 112a ... 112n, and the components illustrated downstream of those amplifiers in circuit 100 are optional in some embodiments.

The components of FIG. 1 may be located on a single substrate or on different substrates. For example, as illustrated, the ultrasonic transducers 102a ... 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a ... 102n and the illustrated circuitry may be monolithically integrated on the same die (e.g., a semiconductor die, such as silicon). Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient, or part of an ultrasound pill to be swallowed by a patient.

As previously described, aspects of the present application provide a multi-stage TIA for an ultrasound device, in which at least two stages of the multi-stage TIA operate with different supply voltages. The inventors have appreciated that the stages of a multi-stage TIA may impact noise performance, linearity, and gain differently. For example, the first stage, electrically closest to the ultrasonic transducer, may dominate noise performance of the TIA, while following (or "subsequent" or "downstream") stages of the TIA may have a greater impact on linearity. Moreover, the reduction of noise achievable with the first stage may depend, at least in part, on the amount of current used in the first stage, with greater current resulting in greater noise reduction. However, since greater current consumption also corresponds with greater power consumption, the inventors have recognized that operating the first stage of a multi-stage TIA at a lower supply voltage may be desirable to reduce the power consumption of that stage. Meanwhile, later stages of the TIA with a greater impact on the linearity of the TIA may be operated at a higher supply voltage level. By using distinct supply voltage levels for the multi-stage TIA, power consumption may be reduced compared to a scenario in which all stages of the multi-stage TIA operate with the same supply voltage level. The closed loop gain may be primarily controlled by the feedback resistance, so long as the open-loop gain bandwidth (the unity gain bandwidth) of the TIA is sufficient.

Figure 2:
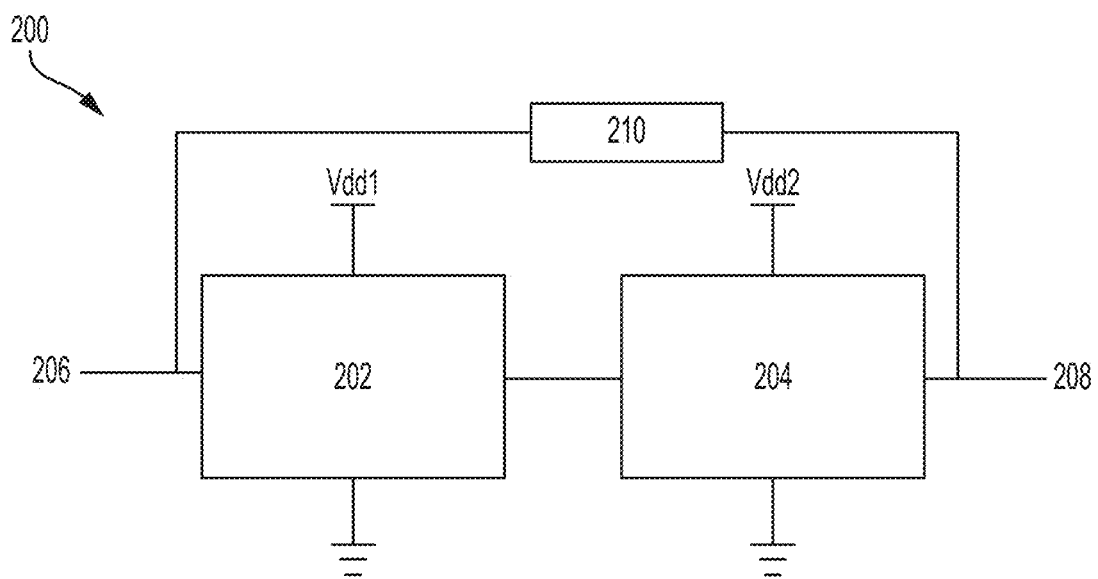
FIG. 2 illustrates a block diagram representation of the amplifier of FIG. 1, illustrating two stages with different supply voltages, according to a non-limiting embodiment of the present application.

FIG. 2 illustrates a non-limiting example of a multi-stage TIA having stages which operate at different supply voltage levels, according to a non-limiting embodiment of the present application. The illustrated TIA may represent one non-limiting implementation of the TIAs 112a . . . 112n of FIG. 1.

As shown, the multi-stage TIA 200 in this non-limiting example includes a first stage 202 and a second stage 204. The first stage 202 may have an input terminal 206 configured to receive an output signal of an ultrasonic transducer. For example, the input terminal 206 may be coupled directly to an ultrasonic transducer or coupled through one or more additional components, such as a receive switch.

The output of the first stage 202 may couple to the input of the second stage 204, and an output signal of the TIA 200 may be provided at the output terminal 208 of the second stage 204.

The multi-stage TIA 200 of FIG. 2 may further comprise a feedback impedance 210. The feedback impedance may be formed by a resistor, capacitor, or combination of impedance elements in some embodiments. The feedback impedance may have any suitable value to provide a target gain of the TIA.

As shown, the first stage 202 and second stage 204 may have respective supply voltages, Vdd1 and Vdd2. The supply voltages Vdd1 and Vdd2 may differ, with Vdd2 greater than Vdd1 in at least some embodiments. As described above, the first stage of the TIA, that is stage 202, may have a greater impact on noise performance of the TIA than the second stage 204, while the second stage 204 may have a greater impact on the linearity of the TIA. Thus, operating the first stage 202 at a lower supply voltage Vdd1 may not negatively impact the linearity of the TIA, but may allow for the first stage 202, and thus the TIA 200, to consume less power for a given level of noise performance.

As should be appreciated from FIG. 2, aspects of the present application provide a multi-stage TIA for an ultrasound device, in which an upstream stage of the multi-stage TIA operates with a lower supply voltage than a downstream stage of the multi-stage TIA. Aspects of the present application provide a multi-stage TIA for an ultrasound device, in which the first stage of the multi-stage TIA operates with a lower supply voltage than a subsequent stage (e.g., a last stage) of the multi-stage TIA.

Figure 3:
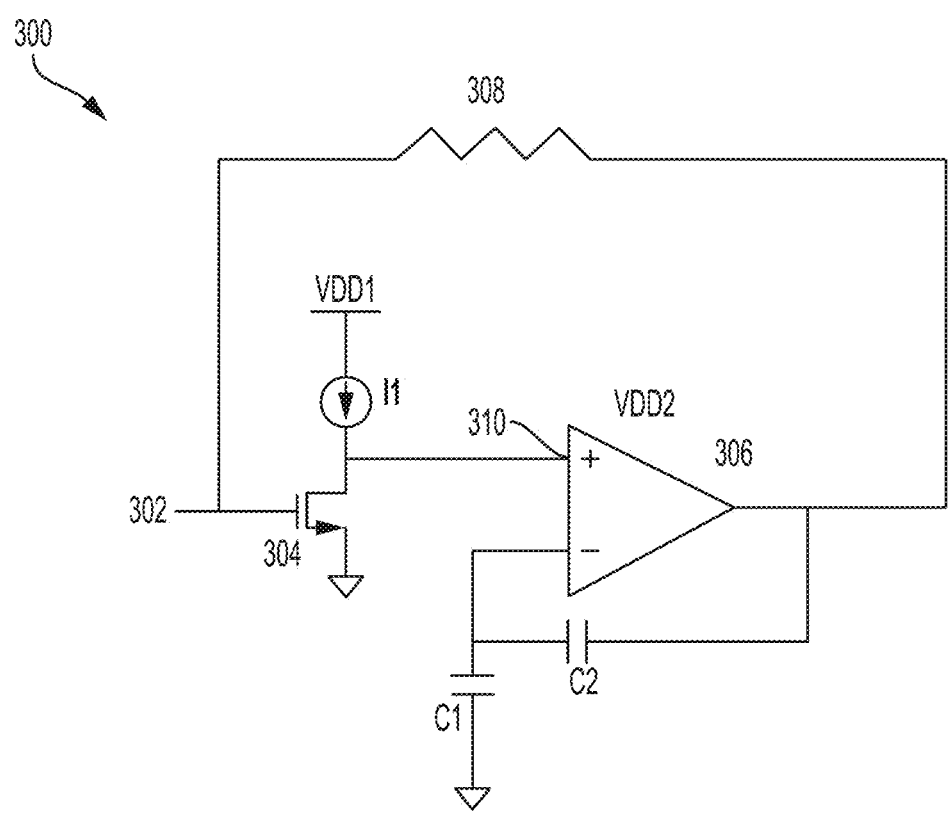
FIG. 3 illustrates a non-limiting example implementation of the multi-stage amplifier of FIG. 2, according to a non-limiting embodiment of the present application.

FIG. 3 illustrates a non-limiting example of an implementation of the multi-stage TIA 200 of FIG. 2. The multi-stage TIA 300 of FIG. 3 comprises an input terminal 302, a first stage comprising a current source I1 and a transistor 304, a second stage comprising an amplifier 306 (e.g., an operational amplifier) and capacitors C1 and C2, and a feedback resistor 308.

As shown, the first stage of the multi-stage TIA 300 may receive a first supply voltage Vdd1, while the second stage may receive a second supply voltage Vdd2. In at least some embodiments, Vdd1 may be less than Vdd2, and in some embodiments is significantly less than Vdd2. For example, Vdd1 may be less than three-quarters of the value of Vdd2, less than half of Vdd2, less than one-quarter of Vdd2, between 25% and 90% of Vdd2, or any other suitable value.

The second stage of the multi-stage TIA 300 may be the dominant factor in controlling the linearity of the TIA. In at least some embodiments, it may be desirable for the TIA to provide a high degree of linearity. The voltage Vdd2 may be selected at least in part to provide a desired degree of linearity.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound apparatus, comprising:
an ultrasonic transducer; and
a multi-stage trans-impedance amplifier (TIA) having an input terminal coupled directly or through one or more components to the ultrasonic transducer and configured to receive and amplify an analog electrical signal from the ultrasonic transducer, the multi-stage TIA comprising multiple stages configured to receive different supply voltages;
wherein the multi-stage TIA includes an upstream stage and a downstream stage, the upstream stage is configured to operate at a first suplly voltage, the downstream stage is configured to operate at a second supply voltage, and the first supply voltage is less than half the second supply voltage.

2. The ultrasound apparatus of claim 1, wherein the ultrasonic transducer and the multi-stage TIA are integrated on a same substrate.

3. The ultrasound apparatus of claim 1, further comprising a switch coupling the multi-stage TIA with the ultrasonic transducer.

4. The ultrasound apparatus of claim 1, further comprising a feedback impedance coupling the downstream stage with the upstream stage.

5. The ultrasound apparatus of claim 1, further comprising filtering and time gain compensation circuitry coupled to the multi-stage TIA.

6. The ultrasound apparatus of claim 1, wherein:
the multi-stage TIA comprises a first multi-stage TIA; and
the ultrasound apparatus further comprises:
  a second multi-stage TIA; and
  an averaging circuit having an input coupled to outputs of the first multi-stage TIA and the second multi-stage TIA.

7. The ultrasound apparatus of claim 1, wherein the first supply voltage is less than one-quarter the second supply voltage.

8. The ultrasound apparatus of claim 1, wherein the upstream stage is a first stage of the multi-stage TIA.

9. The ultrasound apparatus of claim 1, wherein the downstream stage is a last stage of the multi-stage amplifier.

10. The ultrasound apparatus of claim 1, wherein the multi-stage TIA is a two-stage TIA with the upstream stage representing a first stage of the two-stage TIA and the downstream stage representing a second stage of the two-stage TIA, wherein the upstream stage configured to operate at a first supply voltage and the downstream stage configured to operate at a second supply voltage are directly coupled to each other, and wherein the ultrasound apparatus further comprises a feedback impedance coupled between an output of the downstream stage and an input of the upstream stage.

11. A method of operating an ultrasound circuit, comprising:
receiving, directly or through one or more components, an electrical signal output by an ultrasonic transducer; and
amplifying, with a multi-stage trans-impedance amplifier (TIA), the electrical signal output by the ultrasonic transducer,
wherein the multi-stage TIA includes an upstream stage and a downstream stage, the upstream stage being configured to operate at a first supply voltage and the downstream stage being configured to operate at a second supply voltage; and
wherein the first supply voltage is less than half the second supply voltage.

12. The method of claim 11, further comprising providing a feedback signal from the downstream stage to the upstream stage.

13. The method of claim 11, further filtering and time gain compensating an output signal of the multi-stage TIA.

14. The method of claim 11, wherein the upstream stage is a first stage of the multi-stage TIA.

15. The method of claim 11, wherein the downstream stage is a last stage of the multi-stage TIA.

16. The method of claim 11, wherein the ultrasonic transducer and the multi-stage TIA are integrated on a same substrate.

17. The method of claim 11, wherein receiving the electrical signal output by the ultrasonic transducer comprises receiving the electrical signal through a switch coupling the multi-stage TIA with the ultrasonic transducer.

18. The method of claim 11, wherein the multi-stage TIA is a two-stage TIA with the upstream stage representing a first stage of the two-stage TIA and the downstream stage representing a second stage of the two-stage TIA, wherein the upstream stage configured to operate at a first supply voltage and the downstream stage configured to operate at a second supply voltage are directly coupled to each other, and wherein the method further comprises providing a feedback signal through a feedback path coupled between an output of the downstream stage and an input of the upstream stage.

19. An ultrasound apparatus, comprising:
an ultrasonic transducer; and
a multi-stage trans-impedance amplifier (TIA) having an input terminal coupled directly or through one or more components to the ultrasonic transducer and configured to receive and amplify an analog electrical signal from the ultrasonic transducer, the multi-stage TIA comprising multiple stages configured to receive different, respective supply voltages;
wherein the multi-stage TIA includes an upstream stage and a downstream stage, the upstream stage is configured to operate at a first respective supply voltage, the downstream stage is configured to operate at a second respective supply voltage, and
wherein the first respective supply voltage is between 25%-50% of the second respective supply voltage.

20. The ultrasound apparatus of claim 19, wherein the multi-stage TIA is a two-stage TIA with the upstream stage representing a first stage of the two-stage TIA and the downstream stage representing a second stage of the two stage TIA, wherein the upstream stage configured to operate at a first respective supply voltage and the downstream stage configured to operate at a second respective supply voltage are directly coupled to each other, and wherein the ultrasound apparatus further comprises a feedback impedance coupled between an output of the downstream stage and the input terminal of the multi-stage TIA.

* * * * *